United States Patent [19]

Maslak et al.

[11] Patent Number: 5,235,986
[45] Date of Patent: Aug. 17, 1993

[54] VARIABLE ORIGIN-VARIABLE ANGLE ACOUSTIC SCANNING METHOD AND APPARATUS FOR A CURVED LINEAR ARRAY

[75] Inventors: Samuel H. Maslak, Woodside; Hugh G. Larsen, Palo Alto; Joel S. Chaffin, Saratoga; Paul E. Chandler, Santa Cruz; Ian A. Galton, Pasadena; Mehebub S. Karmali, Fremont, all of Calif.

[73] Assignee: Acuson Corporation, Mountain View, Calif.

[21] Appl. No.: 743,915

[22] Filed: Aug. 12, 1991

Related U.S. Application Data

[63] Continuation-in-part of Ser. No. 552,019, Jul. 13, 1990, Pat. No. 5,148,810, which is a continuation-in-part of Ser. No. 478,573, Feb. 12, 1990, abandoned.

[51] Int. Cl.⁵ .............................................. A61B 8/00
[52] U.S. Cl. .................. 128/661.01; 73/625
[58] Field of Search ......... 128/660.01, 660.06–660.07; 73/625–626

[56] References Cited

U.S. PATENT DOCUMENTS

| | | | |
|---|---|---|---|
| 4,344,327 | 8/1982 | Yoshikawa et al. | 73/626 |
| 4,368,643 | 1/1983 | Tachita et al. | 73/626 |
| 4,462,092 | 7/1984 | Kawabuchi et al. | 73/626 X |
| 4,470,308 | 9/1984 | Hayakawa et al. | 73/626 X |
| 4,576,045 | 3/1986 | Miller-Jones | 73/626 |
| 4,582,065 | 4/1986 | Adams | 73/626 X |
| 5,027,659 | 7/1991 | Bele et al. | 73/626 |
| 5,060,652 | 10/1991 | Umemura et al. | 73/626 X |
| 5,148,810 | 9/1992 | Maslak et al. | 128/661.01 |

Primary Examiner—Francis Jaworski
Attorney, Agent, or Firm—James F. Mitchell

[57] ABSTRACT

An acoustic scanning method and apparatus implemented by transmitting ultrasonic pressure waves and receiving return echoes on a set of spatially non-overlapping acoustic lines scanned along a curved linear transducer array with the active acoustic lines shifted and steered so that each acoustic line originates at an arbitrary point on and at an arbitrary angle to the face of the array. In a preferred embodiment, an extension of each acoustic line may also pass through a substantially common vertex that is a selectable distance behind the array to provide a field-of-view defined by the selectively variable location of the common vertex and the physical ends of the array, may use the entire transducer array in the near-field, has high quality resolution in both near and far fields, and may simultaneously transmit and receive two or more ultrasound beams from the same transducer aperture.

19 Claims, 4 Drawing Sheets

VARIABLE ORIGIN-VARIABLE ANGLE ACOUSTIC SCANNING METHOD AND APPARATUS FOR A CURVED LINEAR ARRAY

This application is a continuation-in-part of application Ser. No. 552,019 filed Jul. 13, 1990, and now U.S. Pat. No. 5,148,810 which in turn is a continuation-in-part of application Ser. No. 478,573 filed Feb. 12, 1990 and now abandoned.

BACKGROUND OF THE INVENTION

This invention relates to ultrasound diagnostic scanning where ultrasonic energy illuminates internal organs of the human body in real time and echoes received from the soft organ tissues are transduced into electrical signals and then processed to form two-dimensional cross-sectional images that are displayed upon a TV monitor or like display device.

Ultrasound systems known as phased arrays have been used for some time for medical imaging and have been described, for example, in U.S. Pat. Nos. 4,140,022 and 4,550,607. Two basic scan and display formats have generally been used in combination with planar linear transducer arrays in which the face of individual transducer elements are positioned in a plane parallel to each other and generally have uniform element spacing.

Two-dimensional images have been formed with planar linear arrays by linear scanning where ultrasonic beams on parallel acoustic lines normal to or at an angle to the face of a transducer array are propagated by single transducer elements or by selected groups of transducer elements shifted across the array. Linear scanning, with parallel lines, has the field of view determined by the physical aperture of the transducer. Its advantage is a large field of view (FOV) near the transducer face. However, a large field of view requires a large physical aperture of active transducer elements which may create problems of access and good skin contact.

The other scan and display format which is typically used for planar linear transducer arrays is a sector. In a sector format, the elements are spaced much closer together, typically at half-wavelength or so intervals. This permits the acoustic scan lines to be steered at angles to the planar array without generating grating lobes and allows both the size of the transducer array to be decreased and the field of view to be increased at deeper depths compared to linear formats.

An analogous method of scanning has been used for non-planar or curved linear arrays where the transducer elements are positioned along an arc with radius of curvature R and the scan format consists of a set of scan lines, each normal to the curved pa face of the transducer array. That format is a consequence of unsteered scan lines which are generated in a way analogous to linearly scanning a planar linear array. The physical characteristics of curved linear arrays define a field of view which is determined by acoustic lines substantially normal to the face of the array. The field of view can be increased by using an array with smaller radius of curvature; however resolution is impaired and thereby degraded as compared to a less curved array. Also, a large field of view in the near-field requires a large aperture of active transducer elements. A large field of view in the far-field requires some combination of a large aperture and/or a smaller radius of curvature with the attendant loss of resolution.

Geometry considerations which apply to planar transducer arrays also apply to curved linear arrays. In applications where little or no "steering" at angles not normal to the transducer face is required, the element-to-element spacing can be large, greater than a wavelength or so. In applications where significant steering is required or desired, the element spacing must be less, on the order of half a wavelength or so. Active aperture width considerations depend upon grating lobe and element rolloff behavior.

All the foregoing display formats, as well as mechanical and waterpath scanning, have the field of view defined completely by the physical characteristics of the array. In none of these prior art scanning formats is the field of view substantially altered by situation-dependent software control.

Earlier applications Ser. Nos. 478,573 and 552,019 describe improvements in scanning and display formats for phased arrays and the disclosures in those applications are incorporated herein by reference. Those improvements are applicable to curved linear arrays and permit steering of scan lines in a particular way which can be used advantageously to increase or reduce the field of view, or can cause an entire family of scan lines to be shifted or rotated in a consistent and useful manner.

SUMMARY OF THE INVENTION

The acoustic scanning method and apparatus of this invention involves the propagation of acoustic pressure waves and the reception of returned echoes on a set of acoustic scan lines which are formed by software control, each independent from one another, each originating at an arbitrary origin on the face of a curved linear transducer array and at an arbitrary angle with respect to a normal to the array at each origin. In a preferred embodiment, each scan line may also be part of a ray which extends through a substantially common variably located vertex that is a selectable distance behind the array. In the embodiments described in detail, for convenience called variable vertex scanning, where the common vertex is behind the curvilinear face of the array a distance less than the radius of curvature of the array, acoustic lines can be steered beyond both ends of the array itself, to extend the field of view at all depths with substantially comparable resolution.

The substantially common vertex may alternatively be behind the transducer array, at a distance greater than the radius of curvature of the array, in which case the field of view is decreased, resulting in scan lines which are more nearly parallel. This might be advantageous, for example, in color Doppler imaging, where it is advantageous to maintain a more nearly constant scan angle across a substantially straight vessel. The variable common vertex need not lie on the centerline of the transducer.

Further, it may be advantageous in "mixed" modes, such as the substantially simultaneous display of B-mode and color Doppler mode, to have one vertex for B-mode scan lines, and a different vertex for color Doppler scan lines. In this case, the B-mode and color Doppler scan lines, in general, are not colinear.

This variable vertex format may advantageously increase or decrease the field-of-view with the same physical transducer array. Each acoustic scan line is independently steered, so that no two scan lines are necessarily parallel to each other. The variable common vertex location may optimize the field of view for a particular transducer geometry. The only constraint is that the steering angle with respect to a normal to the transducer elements may not be greater than the greatest permitted for a sector scan line for the same transducer element spacing. This criterion is determined by an acceptable grating lobe amplitude. A conservative criterion which effectively suppresses grating lobes limits the steering angle $\Theta_o$ as follows:

$$|\theta_0| \leq \sin^{-1}\left(\frac{\lambda}{d} - 1\right), d \geq \frac{\lambda}{2}$$

where $\lambda$ is the transducer center-frequency wavelength and d is the element spacing. This criterion keeps the center of any grating lobe at an angle of at least $-90°$ with respect to the previously mentioned normal. Greater steering angles can be used where the array elements have sufficient directivity. A gradual lowering of the center-frequency, increasing the wavelength, as the array is steered away from normal suppresses grating lobes so as to permit greater steering angles, too.

The scanning method of this invention is general and accommodates many array physical geometries. Scanning a curved or general curvilinear array of transducer elements is enabled simply by fomring independent acoustic scan lines at arbitrary points of origin on the face of the array steered to an arbitrary angle with respect to a normal to the array at the scan line origin. The acoustic lines preferably are selected to be spatially non-overlapping in the entire field of view to accommodate operation with multiple simultaneous acoustic beams for improved frame rate or simultaneous Doppler and image scanning. Shifting and steering of each active acoustic line is software-programmable to optimize the field of view for variations in transducer operating frequency or to respond dynamically to situation-dependent phenomena such as presence of obstructions in the field of view (ribs, for example).

The substantially common vertex of the preferred embodiment is a special case of this invention. More generally, this invention describes a method of scanning a curved or general curvilinear array of transducers in which substantially each scan line originates from an arbitrary but different location on the transducer array and substantially each scan line might be steered to a different angle with respect to the normal to the array at the point of origin of the scan line.

DESCRIPTION OF THE PREFERRED EMBODIMENTS

Figure 1:
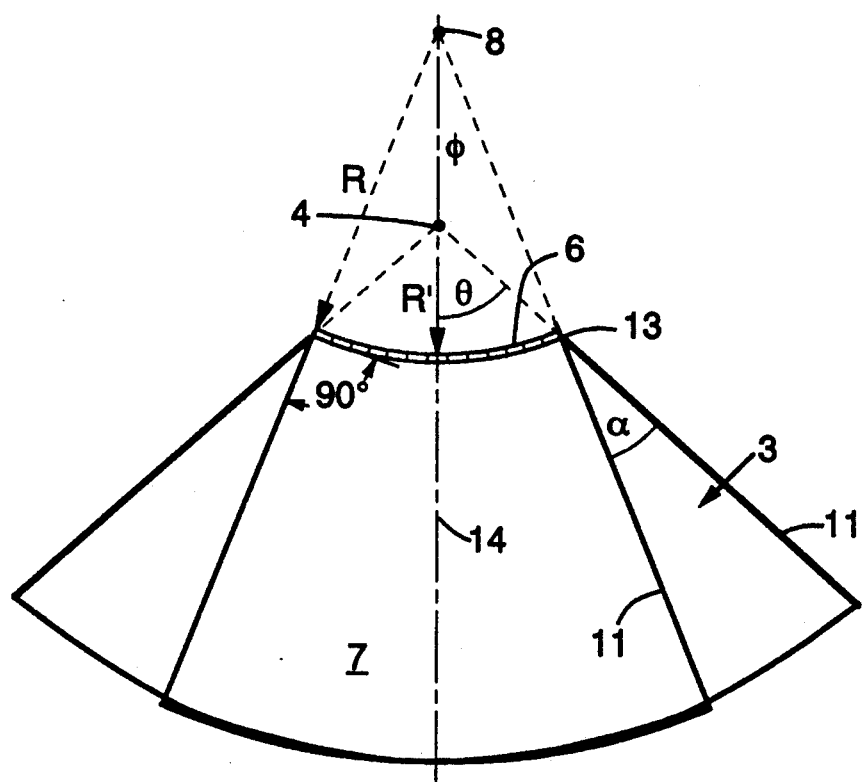
FIG. 1 illustrates the image plane formed by a curved linear transducer array with a variable vertex format superimposed upon it having a radius less than the radius of curvature of the array.

FIG. 1 illustrates a curved linear transducer array 6 and the field of view 7 obtained by multiple acoustic lines propagated normal to the face of the transducer array. Extensions of these normal acoustic lines pass through a common center of curvature 8. The field of view for the curved linear transducer array can be expanded into the variable vertex format 3 by a set of acoustic lines propagated at varying angles to the face of the curved linear array, extensions of which all pass through common vertex 4, where that common vertex is preferably between the center of curvature 8 and the face of the array.

For a curved linear array, each acoustic scan line 11 originates from a different arbitrary point 13 on the face of the curvilinear array. These points of origin can be described by the angle $\phi$, the center of curvature 8 and the centerline of the transducer array 14. Alternately, in the variable vertex format each origin 13 for the ultrasound lines can be described by the angle $\Theta$, the common variable vertex 4 and the centerline 14 connecting variable vertex 4 to the center of curvature 8 of the array As shown in FIG. 1, each acoustic line for the variable vertex format is steered at the angle $\alpha$ with respect to the normal to the face of the curvilinear array. In FIG. 1 the center of curvature 8 is on the centerline 14 of the transducer array and the angle $\alpha$ equals the angle $\Theta$ less the angle $\phi$. The delay equations for focused scanning with a curvilinear transducer array can be derived using these angular relationships and the location of the common vertex 4 relative to the radius of curvature 8 as is described in connection with FIGS. 4,5.

Figure 3:
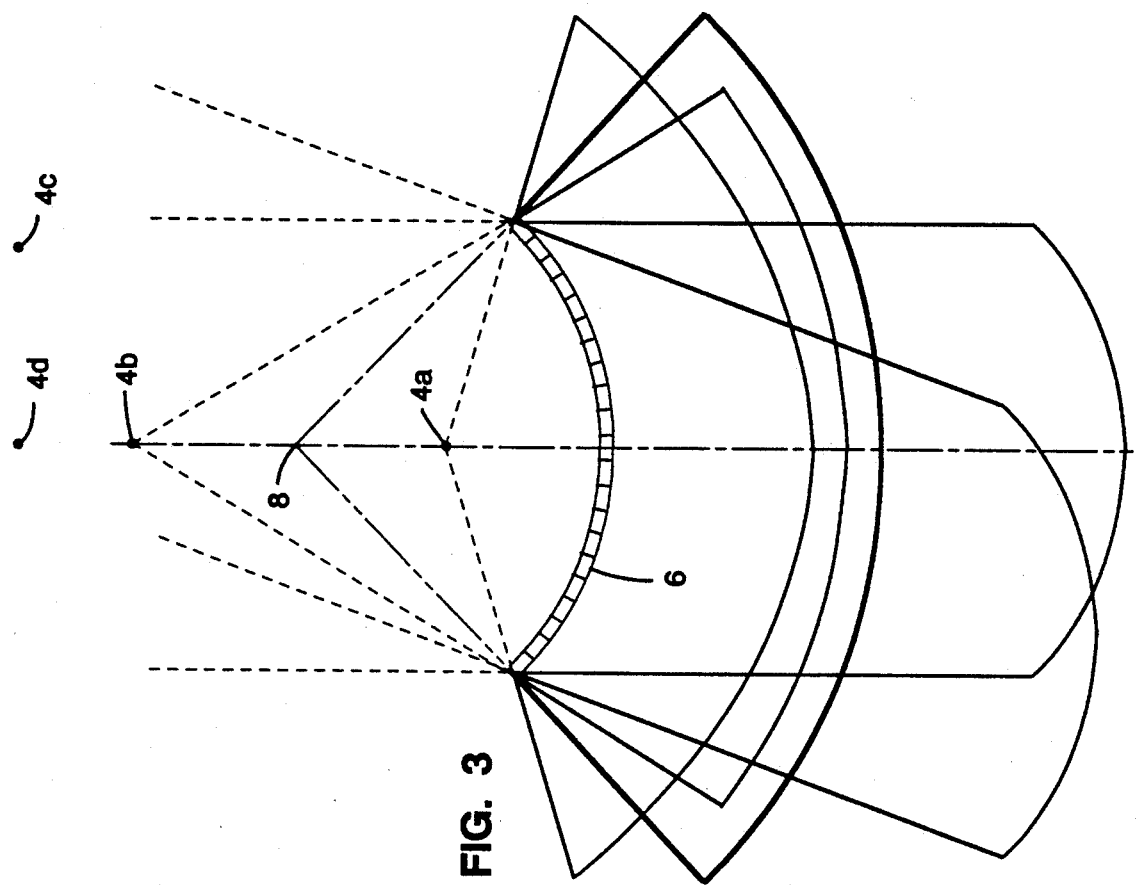
FIG. 3 illustrates a variable vertex format for a curved linear transducer array with five different placements of a common vertex including two examples of essentially parallel scan lines with common vertex at infinity.
Figure 2:
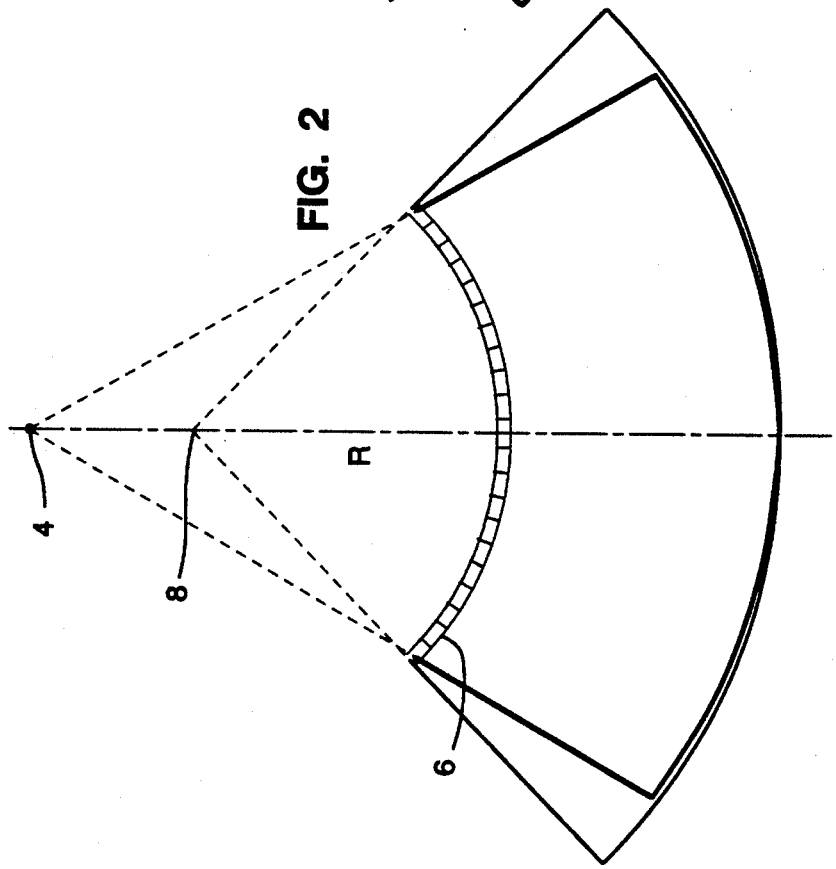
FIG. 2 illustrates a variable vertex format for a curved linear transducer array with a common vertex at a radius greater than the radius of curvature.

An expanded field of view might be a major advantage in some imaging applications where, for example, it might be important to include an entire organ or several organs in the body in the same image. The variable vertex 4 also may be located at a radius behind the array that is greater than the radius of curvature R from the array center 8 as shown in FIG. 2. So, too, can the variable vertex be placed at any location behind the array such as at 4a or 4b or at infinity 4c, 4d shown in FIG. 3. It might be useful to reduce the field of view (FOV) in order to achieve more nearly parallel scan lines in mixed B-mode and color Doppler modes. In this instance, one scanned FOV as shown in either FIG. 1 or FIG. 2 might be used to display B-mode information, in combination with a reduced FOV color Doppler information superimposed on it. The advantage of this is that, if the angle of incidence of all scan lines is more nearly the same across a nominally straight blood vessel, then a more accurate representation of color encoded velocity information is possible. The ability to completely cover the B-mode image is insured by the variable moving vertex, as shown in FIG. 3.

Variable vertex scanning, as described here, is a generalization of which sector scanning is a special case.

Linear scanning, meaning scanning with a planar linear transducer wherein all scan lines are normal to the transducer, is analogous to curved linear array scanning as shown in FIG. 1, where the scan lines are also normal to the surface of the transducer. In both cases, the scan and display format follow the natural shape of the transducer, and both of these are well-known to the present state of the art. Sector scanning, as has been practiced by the present state of the art, requires that all scan lines intersect at a common point which is on the face of the transducer, typically being a planar linear array. Variable vertex scanning includes either planar or curved linear transducer scanning where the point of origin of the scan lines typically but not necessarily is common, and when common its location is arbitrary. Typical cases where there is no common point of intersection of the scan lines is when the scan lines are precisely parallel, or where each scan line forms a common angle with respect to a normal to the array, or where two or more, but not all, scan lines intersect in a common point or where none intersect at all.

A principal objective of this invention is to define a scan and display format for an imaging system for which the common vertex 4 of all acoustic scan lines can be selectively positioned at any point within the scan plane. As illustrated in FIG. 1, the variable vertex 4 is on a reference line 14 normal to an arc connecting all transducer elements of the physical aperture of the array 6 at a distance R' behind the face of the array. However, the position of the variable vertex is arbitrary and can be at 4a, 4b, 4c or 4d, for example, as shown in FIG. 3.

The format applies equally well to spectral Doppler and color flow Doppler imaging as well as to B-mode imaging. In particular, certain mixed modes enhance the utility of variable vertex scan and display format. Examples include: (1) the variable vertex 4a scan format in 2-D in combination with substantially parallel color flow scan lines, shown in FIG. 3 from a remote vertex 4c, (2) multiple pulsed Doppler scan lines with variable vertices that are distinct from each other in combination with a 2-D image or other combinations that would be readily apparent to persons skilled in the art.

Figure 5:
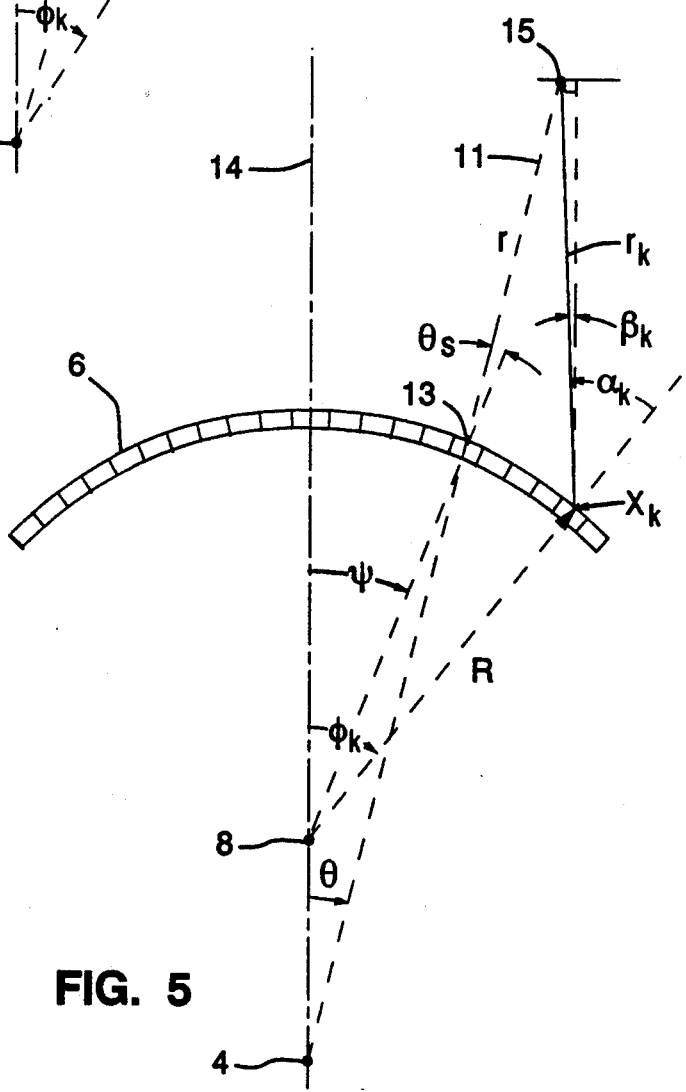
FIG. 5 is a schematic diagram from which delay transformation equations are developed for any arbitrary transducer element in the variable vertex format for a curved linear array.

Included in this invention is the means to select an origin 13, as shown in FIG. 5, and focal point 15 for a particular ultrasound beam such that the acoustic scan line 11 appears to originate at or emanate from the common vertex 4. The actual origin of an ultrasound beam occurs on a line connecting the individual transducer elements at the point corresponding approximately to the center of mass of its apodization function Equation (A) is used to manage the apodization function which may or may not include a factor due to element rolloff compensation such that its center of mass is equivalent to or nearly equivalent to the intended origin 13 of the acoustic scan line 11. The origin of the beam therefore can be controlled by simply shifting this center of mass. The shift required to place the beam origin at or near the intersection 13 of an arc connecting all elements of the transducer on the face of the array with an acoustic scan line 11 which connects the variable vertex 4 to the focal point, as at 15, depends upon the spatial position of the variable vertex and the steering angle $\Theta_s$.

Figure 4:
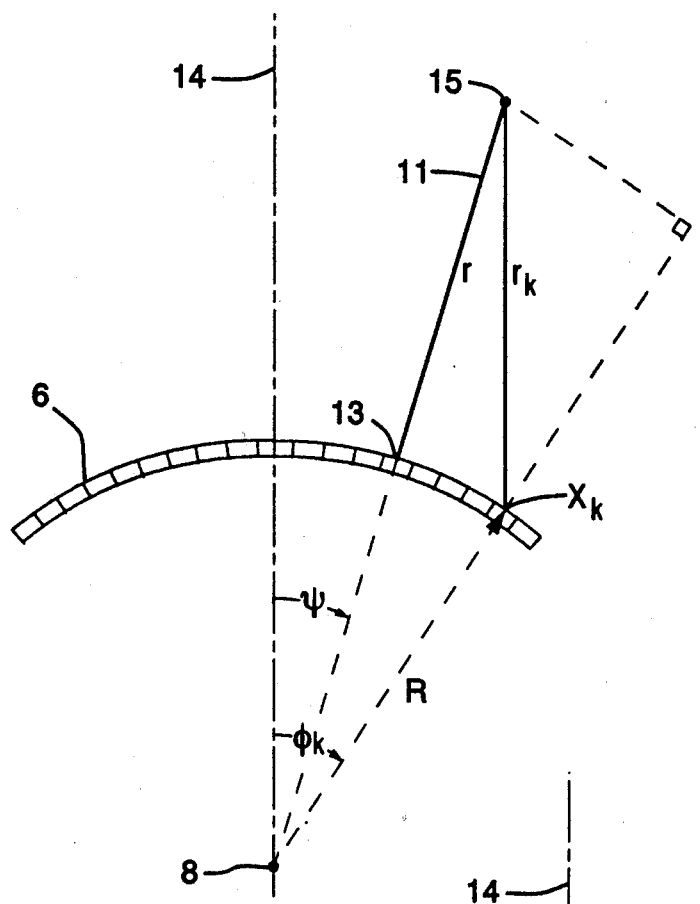
FIG. 4 is a schematic diagram from which delay equations are developed for a conventional curved linear array scanning format with scan lines normal to the array.

An ultrasound beam originates from approximately the center of mass, $X_{cm}$ of its apodization function where $X_{cm}$ is measured along the arc of the transducer face. The apodization function $A(X_k)$, may be described as the weighting given to the signal transmitted from, or received from, an element at position $X_k$. Referring to FIG. 4, $X_k = R \cdot \phi_k$, and $$X_{cm} = \frac{\sum_{k=0}^{L} \int_0^{X_L} X \cdot A(X) \cdot \delta(X - X_k) \cdot dX}{\sum_{k=0}^{L} \int_0^{X_L} A(X) \cdot \delta(X - X_k) \cdot dX} \quad (A)$$

where $\delta(x)$ is the Dirac delta function and has the property that $$\int_{-\infty}^{\infty} f(X) \cdot \delta(X - X_k) \cdot dX = f(X_k)$$

Controlling the ultrasound beam origin is achieved by assigning the apodization values to each element of the physical transducer array in such a way that the center of mass $X_{cm}$ corresponds approximately to the ultrasound scan line origin 13. There is no requirement that $X_{cm}$ corresponds to an element position. In principle, the center of mass is computed for each acoustic scan line 11 and a unique apodization profile is generated for each scan line. In actual practice, only a limited set of profiles are required by taking the shift invariance property of the apodization profile into account. This means that, for example, one can cause the center of mass to shift by exactly one element spacing by simply shifting the assignment of each apodization value from the $k^{th}$ element to the $(k+1)^{th}$ element. This operation is easy to accomplish by means of control logic in combination with a microprocessor during the quiescent period between successive acoustic scan lines. Another unique set of apodization profiles is required to shift the center of mass by a fraction of an element spacing. Typically the position of the center of mass (and therefore the ultrasound line origin) is controlled to within about one-quarter of a wavelength for foci close to the transducer array. All other combinations required for each unique ultrasound scan line are obtained by simple shift operations applied to one of these sets.

A non-steered curved linear array scan line 11 is shown schematically in FIG. 4 where the time delay required at the $k^{th}$ element is calculated in order to have a focus at range r, as at focal point 15, along acoustic scan line 11 from the face of the transducer array 6 for angle $\psi$ with respect to a reference line 14. The radius of curvature is R for the array. The angle $\psi$ is formed by the intersection of two lines, reference line 14 and scan line 11 extended back through the center of curvature 8 of the array, also normal to the array at the scan line origin 13. In the prior art, scan lines are always substantially normal to the curved transducer array at the ultrasound scan line origin 13, as shown in FIG. 4.

Consider now an active element k which contributes energy to the focal point 15 that is at a distance r from the origin 13 along the scan line 11. The propagation time delay at element k relative to the propagation time delay at the scan line origin 13 is given by $$T_k = \frac{1}{c}[r - r_k] \quad (1)$$

From the reconstruction shown in FIG. 4:

$$r_k^2 = [(r+R)\cos(\phi_k-\psi)-R]^2 + [(R+r)\sin(\phi_k-\psi)]^2 \quad (2)$$

from which:

$$r_k = r\left\{1 + 2\frac{R^2}{r^2}\left[1 + \frac{r}{R}\right](1 - \cos(\phi_k - \psi))\right\}^{\frac{1}{2}} \quad (3)$$

where:
c = the velocity of sound in the body = 1.54 mm/sec
r = the distance from the usl origin 13 to the focal point 15
$r_k$ = the distance from the $k^{th}$ element to the focal point 15

If $T_k<0$, echoes arrive at the scan line origin 13 before arriving at the $k^{th}$ element, whereas if $T_k<0$, echoes must be delayed at the $k^{th}$ element prior to coherent summation with echoes arriving at the scan line origin 13. In general, the delay applied at the $k^{th}$ element must be $T_k+T_o$, where $T_o$ represents an arbitrary delay offset necessary to insure that all delays are positive and therefore realizable. The delays may be quantized as is known in the prior art.

Since $r_k$ and therefore $T_k$ is a function of the range r and angle $(\phi_k-\psi)$, we can generate one scan line from previous scan lines by choosing $\psi$ to be integer or submultiples of the element angular spacing $\Delta\phi$, where $\phi_k = k \cdot \Delta\phi$, and $\Delta\phi$ is the interelement angular spacing. The delay data must be re-ordered from scan line to scan line, as is well-known in the prior art. In FIG. 5, the scan line 11 is no longer at normal incidence with respect to the curved linear array at the scan line origin 13. An extension of the scan line 11 back through the array intersects with a normal line through the physical center of the curved linear array at some angle $\Theta$ at a point, called the variable vertex 4, which does not correspond to the center of curvature 8 of the array. The angle which the scan line 11 makes with respect to a normal to the array at the scan line origin 13 is $\Theta_s$, which may be viewed as a steering angle. A complete description of the symbols shown in FIG. 5 is as follows:

$\psi$ = the angle formed by the intersections of the reference line 14 and a normal line through the scan line origin 13 intersecting the reference line at the center of curvature 8 of the array.

$\Theta$ = the angle formed by the intersection of the reference line 14 and an extension of the scan line 11 at the variable vertex 4.

$\Theta_s$ = the steering angle with respect to the normal at the scan line origin 13. $\Theta_s$ is negative when the variable vertex 4 is beyond the center of curvature, as shown in FIG. 5.

$\phi_k$ = the angle formed by the reference line 14 and a normal line through the $k^{th}$ element, intersecting at the center of curvature 8 of the array.

$\alpha_k$ = the acceptance angle of the $k^{th}$ element, which is defined as the angle formed by the normal at the $k^{th}$ element and the line whose length is $r_k$, connecting the $k^{th}$ element to the focal point 15.

$\beta_k = \Delta\alpha_k - \phi_k$

In order to compute the propagation delay $T_k$ from the geometry of FIG. 5, one first computes $r_k$. From FIG. 5

$$r_k \sin\beta_k = R\sin\phi_k - R\sin\psi - r\sin\theta \quad (4)$$

$$r_k \cos\theta + R\cos\psi - R\cos\phi_k \quad (5)$$

Squaring both sides of (4) and (5), then summing gives:

$$r_k = r\left\{1 + 2\frac{R^2}{r^2}\left[(1-\cos(\phi_k-\psi))\cdot\left(1+\frac{r}{R}\cos\theta_s\right) - \frac{r}{R}\sin(\phi_k-\psi)\cdot(\sin\theta_s)\right]\right\}^{\frac{1}{2}} \quad (6)$$

The active aperture of individual transducer elements is managed by limiting the absolute acceptance angle $\alpha_k$, to be less than some upper limit. For example, if the acceptance angle for the $k^{th}$ element $|\alpha_k| \geq 90°$, then that $k^{th}$ element contributes no useful echo for imaging. As such, according to FIG. 5, the acceptance angle is given by $$\sin\alpha_k = \frac{R}{r_k}\left[\sin(\phi_k-\psi)\cdot\left(1+\frac{r}{R}\cos\theta_s\right)\right] - \frac{r}{r_k}\cos(\phi_k-\psi)\cdot\sin\theta_s \quad (7)$$

Approximate Delay Equations

Equation (6) discloses how to compute the delays for an imaging system with a single fixed focal point along a ray with steering angle $\Theta_s$ and scan line origin at a distance $R\cdot\psi$ along the physical array from reference line 14 with respect to a focal point 15. One such set of delays (one value per element position) is uniquely required for each acoustic scan line.

Means to achieve dynamic focusing may be obtained by simply generalizing equation (6) to include a family of focal ranges, rather than a fixed focal range, r. This constitutes a significantly large data set. That is, the amount of delay data required to achieve a fixed focus is given by

[Number of delay values] = [N active transducer elements]·[M scan lines] = N·M delay values In the case of mirror symmetry of the scan lines about a reference scan line, M is replaced by M/2 scan lines.

For a dynamically focused imaging system, with K focal ranges, this becomes (K·N·M) delay values. For a high performance ultrasound imaging system with 128 active transducer elements, this amounts to approximately 3·10⁵ delay values. As a result means to reduce the amount of high-speed RAM is a desired objective.

Figure 6:
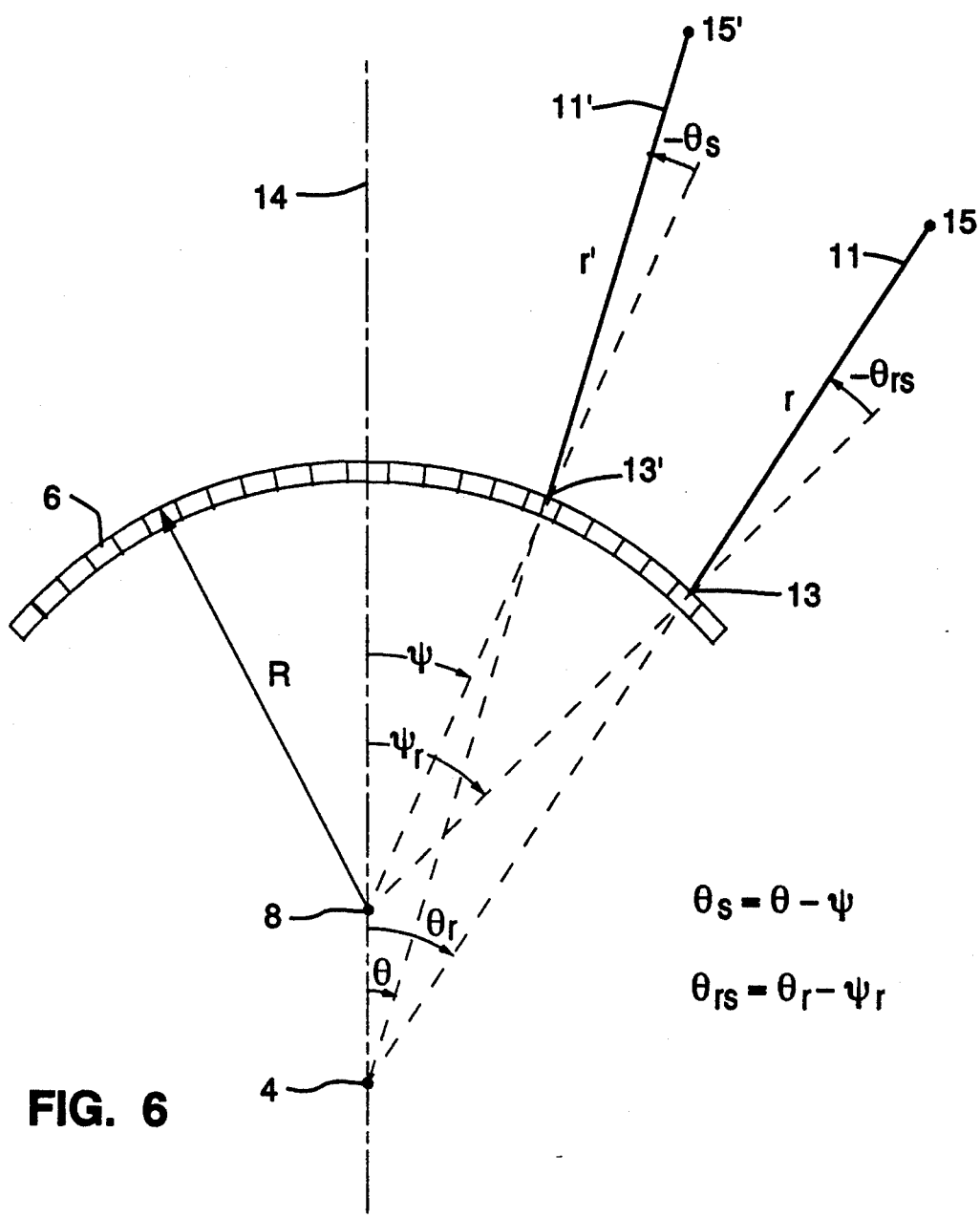
FIG. 6 schematically illustrates decomposition of delay equation terms into reference and variable components.

Data reduction can be achieved by means of a decomposition of the delay equation (1) with equation (6) substituted for $r_k$ into a reference (fixed) focus and a variance focus term illustrated in FIG. 6 for scan lines 11 and 11'. The approximation selected for the described embodiment is expressed as follows:

If the delay to the $k^{th}$ element is given by $$T_k = (r - r_k)/C = T(r, \phi_k-\psi, \Theta_s, R) \quad (8)$$

where $T_k$ is obtained by substituting equation (6) for $r_k$, then $T_k$ can be approximated to good accuracy by considering $$T_{Ak} = T(\rho, \phi_k-\psi, \Theta_s, R) + [T(r, \phi_k-\psi_r, \Theta_r, R) - T(\rho, \phi_k-\psi_r, \Theta_r, R)] \quad (9)$$

where:
 ρ = a fixed reference focus
 $\Theta_{rs}$ = a fixed reference steering angle as shown in FIG. 6
 $\Theta_r$ = a reference angle as shown in FIG. 6

$$T(\rho, \phi_k-\psi, \Theta_s, R) = a \text{ reference (fixed) focus term} \quad (10)$$

$$T(r, \phi_k-\psi_r, \Theta_r, R) - T(\rho_1\phi_k-\psi_r, \Theta_r, R) = a \text{ variable focus term} \quad (11)$$

where r can take on many values.

As has been discussed in application 552,019, $T_{Ak}$ approximates $T_k$ to high accuracy provided that ρ is selected approximately in the middle of the range, r, of focal ranges of interest; and steering angles $\Theta_s$ vary by no more than ±12.5° or so from the reference steering angle $\Theta_{rs}$. For situations requiring a large range of steering angles, one simply generates another family of variable focus terms with a different reference angle This may be extended as required.

The variable focus term has a very weak effect on steering. One can align the origin of the variable focus term with that of the fixed focus term by recognizing that $$R(\phi_k-\psi) - R(\phi_k-\psi_r) = R(\psi_r-\psi) = m \cdot d - \epsilon \quad (12)$$

where
 d = the interelement spacing
 m = some integer
 ε = a fractional remainder If ε = 0, then the delay required to generate equation (7) from one scan line to another (in the range of $\Theta_s$ for which the reference angle $\Theta_{rs}$ is valid) is generated by simply reassigning the delay value associated with the $k^{th}$ element to the $(k+m)^{th}$ element.

Figure 7:
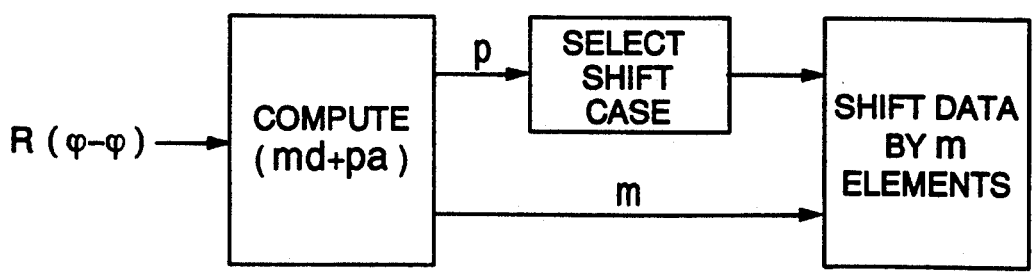
FIG. 7 schematically illustrates the selection and shifting of the delay data used for propagating the acoustic scan lines.

Since, in general ε does not equal 0, then one must have additional sets of delay values corresponding to the variable focus term characterized by equation (11). If one defines the number of shift cases, p, such that $\epsilon = p \cdot a$, and $a/2$ is the greatest positional error which one is willing to accept, then one can re-write equation (12) with the variable change $$R(\psi-\psi_r) = m \cdot d + p \cdot a \quad (13)$$

where m and p are now control variables which are used as indices into the delay value data tables, and m is the number of single element delay value data positions by which the data must be shifted before it is applied. This is represented schematically in FIG. 7.

The foregoing shows how the delay calculations may be efficiently generated and implemented to accommodate variable vertex scanning for a curved linear array. However, one might alternatively generate this data in a straightforward way as well, since efficient generation means is not essential to the disclosed invention. Means by which the delay calculations are implemented to accommodate systems that employ heterodyning means in combination with coarsely quantized delay lines to achieve dynamic focussing as described in U.S. Pat. Nos. 4,140,022 and 4,550,607 follow in a straight-forward manner as is described in application Ser. No. 552,019.

We claim:

1. A method for scanning a non-planar array of individual transducer elements for obtaining image, velocity or variance data from a section of a body comprising the steps of propagating acoustic pressure waves into the body from at least one active transmit aperture of individual transducer elements, receiving acoustic echoes on a set of acoustic lines, which are spatially non-overlapping using for each line a variable active aperture of individual transducer elements which may selectively include only some or all elements of the array, shifting on transmission or receive each acoustic line to originate from an arbitrary origin at the face of said transducer array, and electronically steering on transmission or receive each acoustic line at an arbitrary angle relative to the face of the array.

2. The method of claim 1 wherein the array is a curved linear array.

3. A method for scanning a curved linear array of individual transducer elements for obtaining image, velocity or variance data from a section of a body comprising the steps of propagating acoustic pressure waves into the body from at least one active transmit aperture of individual transducer elements, receiving acoustic echoes on a set of acoustic lines, which are spatially non-overlapping using for each line a variable active aperture of individual transducer elements which may selectively include only some or all elements of the array, and electronically steering the angle of each acoustic line relative to the array so that an extension of the acoustic line in space beyond its origin at the array passes through a substantially common vertex which is not located at the center of curvature of the transducer array.

4. The method of claim 3 wherein said common vertex is located a selectable distance in space behind the transducer array so as to provide a selectable field-of-view of said body.

5. The method of claim 3 wherein said common vertex is located a selectable distance in space in front of the transducer array and the acoustic lines overlap only at the common vertex.

6. The method of claim 3 further including the step during reception of dynamically focussing along each acoustic line.

7. The method of claim 3 further including the step during reception of dynamically adjusting the size or center of the aperture of active transducer elements of the array.

8. The method of claim 7 wherein the size of said aperture is a function of the acceptance angle of end transducers in the aperture.

9. The method of claim 3 wherein the shape of apodization is dynamically varied during reception along each scan line.

10. Apparatus for obtaining image, velocity or variance data from a section of a body on a set of acoustic lines scanned along a non-planar transducer array with each acoustic line originating on the array at an arbitrary origin comprising an array of individual transducer elements placed against the body, means for propagating acoustic pressure waves into the body from at least one active transmit aperture of individual transducer elements in the array, means for receiving acoustic echoes on a set of acoustic lines which are spatially non-overlapping using a variable active aperture of individual transducer elements which may selectively include only some or all elements of the array, means for originating substantially all acoustic lines from a different arbitrary origin at said transducer array within the active aperture, and means for electronically steering substantially all acoustic lines at an arbitrary angle relative to the face of the array.

11. The apparatus of claim 10 wherein the active transmit aperture of individual transducer elements is selectively variable to include only some or all elements of the array.

12. The apparatus of claim 10 wherein the number of individual transducer elements in the active aperture for propagating said pressure waves may differ from the number of elements in the active aperture which receives the acoustic echoes at each depth in the field-of-view.

13. The apparatus of claim 10 wherein the transducer array is a curvilinear array and substantially all acoustic lines are steered at a direction which is not normal to the curved face of the array.

14. The apparatus of claim 13 wherein extensions of said acoustic lines in space pass through a common vertex located between the center of curvature of the transducer array and the face of the array.

15. The apparatus of claim 13 wherein extensions of said acoustic lines in space pass through a common vertex at a distance from the array that is greater than the radius of curvature of said array and behind said array.

16. Apparatus for obtaining image, velocity or variance data from a section of a body on a set of acoustic lines scanned along a non-planar transducer array with each acoustic line originating on the array at an arbitrary origin relative to the center of the face of the array, comprising an array of individual transducer elements adapted to be placed against the body, means for propagating acoustic pressure waves into the body from at least one active transmit aperture of individual transducer elements in the array, means for receiving acoustic echoes on a set of acoustic lines which are spatially non-overlapping including means for forming a variable active aperture of individual transducer elements which selectively includes only some or all elements of the array, means for originating substantially all acoustic lines from a different arbitrary origin at said transducer array within the active aperture, and means for electronically steering substantially all acoustic lines at an arbitrary angle relative to the face of the array.

17. The apparatus of claim 16 wherein the transducer array is a curvilinear array and substantially all acoustic lines are steered at an angle which is not normal to the curvilinear face of the array.

18. The apparatus of claim 17 wherein extensions of said acoustic lines in space pass through a common vertex between the center of curvature of the transducer array and the face of the array.

19. The apparatus of claim 17 wherein extensions of said acoustic lines in space pass through a common vertex at a distance from the transducer array that is greater than the radius of curvature of said array and behind said array.

* * * * *